United States Patent
Akhtar et al.

(10) Patent No.: US 11,286,467 B1
(45) Date of Patent: Mar. 29, 2022

(54) SYSTEM AND METHOD FOR PRODUCTION OF FATTY ACID ETHANOLAMIDES

(71) Applicant: UNITED ARAB EMIRATES UNIVERSITY, Al Ain (AE)

(72) Inventors: Mohammed Kalim Akhtar, Al Ain (AE); Dhanya Vijay, Al Ain (AE)

(73) Assignee: UNITED ARAB EMIRATES UNIVERSITY, Al Ain (AE)

(*) Notice: Subject to any disclaimer, the term of this patent is extended or adjusted under 35 U.S.C. 154(b) by 0 days.

(21) Appl. No.: 17/121,569

(22) Filed: Dec. 14, 2020

(51) Int. Cl.
*C12N 9/16* (2006.01)
*A61K 35/741* (2015.01)
*C12N 9/10* (2006.01)
*C12N 15/70* (2006.01)

(52) U.S. Cl.
CPC .............. *C12N 9/16* (2013.01); *A61K 35/741* (2013.01); *C12N 9/1029* (2013.01); *C12N 15/70* (2013.01); *C12Y 203/01086* (2013.01); *C12Y 301/04054* (2013.01)

(58) Field of Classification Search
None
See application file for complete search history.

(56) References Cited

U.S. PATENT DOCUMENTS

| | | |
|---|---|---|
| 9,683,247 B2 | 6/2017 | Lutes et al. |
| 9,795,640 B2 | 10/2017 | Davies et al. |
| 2021/0171987 A1* | 6/2021 | Keasling ............... C10L 1/026 |

FOREIGN PATENT DOCUMENTS

| | | |
|---|---|---|
| EP | 3040070 A1 | 7/2016 |
| WO | 2016210378 A2 | 12/2016 |
| WO | 2017123418 A1 | 7/2017 |

OTHER PUBLICATIONS

Chen, Z. et al., "Incorporation of therapeutically modified bacteria into gut microbiota inhibits obesity," Journal of Clinical Investigation, vol. 124, No. 8, pp. 3391-3406, Aug. 2014.

Dosoky, N. S. et al., "Dietary Fatty Acids Control the Species of N-Acyl-Phosphatidylethanolamines Synthesized by Therapeutically Modified Bacteria in the Intestinal Tract," ACS Infectious Diseases, 2018, 4, pp. 3-13.

May-Zhang, L. S. et al., "Administration of N-Acyl-Phosphatidylethanolamine Expressing Bacteria to Low Density Lipoprotein Receptor -/- Mice Improves Indices of Cardiometabolic Disease," Scientific Reports, 9:420, Jan. 23, 2019.

* cited by examiner

*Primary Examiner* — Suzanne M Noakes
*Assistant Examiner* — Jae W Lee
(74) *Attorney, Agent, or Firm* — Nath, Goldberg & Meyer; Richard C. Litman

(57) ABSTRACT

A system and method for production of fatty acid ethanolamides (FAEs) are provided. The system and method for production of fatty acid ethanolamides includes microbes engineered to express the necessary enzymes to complete a FAE biosynthetic pathway, resulting in the conversion of glucose to one or more desired FAEs. The microbes may be engineered to express at least two of thioesterase, fatty acyl CoA synthase, NAPE-synthase, and NAPE phospholipase-D. The FAE-producing microbes can be administered to a subject in need thereof as part of a probiotic regimen.

13 Claims, 5 Drawing Sheets

SYSTEM AND METHOD FOR PRODUCTION OF FATTY ACID ETHANOLAMIDES

BACKGROUND

1. Field

The disclosure of the present patent application relates to fatty acid ethanolamides, and particularly to a system and method for production of fatty acid ethanolamides.

2. Description of the Related Art

Fatty acid ethanolamides (FAEs) are found in plants and animals where they play a role in cellular signaling. FAEs have been of interest to researchers since the 1950s, when palmitoyl ethanolamide was identified as an anti-inflammatory factor. Palmitoyl ethanolamide is also known to have anti-nociceptive, neuroprotective, and anticonvulsant properties. Another FAE, stearoylethanolamide, has been shown to have anti-inflammatory, apoptotic, and anorexic effects. A further FAE, Oleoylethanolamide, is of particular interest as a potential target for anti-obesity therapies. Oleoylethanolamide has been shown to inhibit adipogenesis in adipose tissues and to activate lipolysis in muscle tissues. Oleoylethanolamide is understood to decrease food intake by inducing the feeling of satiety, possibly through interaction with peroxisome proliferator-activated reception (PPAR-alpha).

Conventional approaches to industrial synthesis of FAEs produce amides synthesized from a fatty acid and ethanolamine. The fatty acid may be extracted from plant materials or sourced from fatty acid chloride, while ethanolamine may be derived from ethylene. The fatty acid and the ethanolamine may then undergo a highly efficient amidation reaction using a lipase enzyme, or the amidation may be achieved via conventional means using fatty acid chlorides as a fatty acyl donor; however, this uses toxic and corrosive materials. The ethylene used in this approach is formed from hydrolytic cracking of petroleum, a resource for which there is a limited supply. The use of fatty acids extracted from plants faces numerous challenges, including yield variability, geographical confinement, high labor costs, varying climactic conditions, and the complexity of the extraction and isolation techniques. Overall, the conventional approaches to FAE production are economically viable but leave a significant ecological footprint and may not be sustainable for long term use.

Thus, a system and method for production of fatty acid ethanolamides solving the aforementioned problems is desired.

SUMMARY

The system and method for production of fatty acid ethanolamides (FAEs) provides for in vivo synthesis of FAEs using engineered microbes and food stocks, e.g., cheap sugar feedstocks, to produce a surplus of FAEs. The microbes are engineered to express the necessary enzymes to complete a FAE biosynthetic pathway, resulting in the conversion of glucose to one or more desired FAEs. The microbes may then be grown in a standard bioreactor, fermenter, or under any known optimized growth conditions to allow for synthesis of the one or more desired FAEs. These FAE-producing microbes can be administered to a subject in need thereof as part of a probiotic regimen. The FAE-producing microbes may be administered to subjects suffering from any condition that the selected FAE is known to have activity against, including but not limited to subjects suffering from obesity or chronic pain.

In an embodiment, the system for production of FAEs may include *E. coli* microbes engineered to express thioesterase (TES), fatty acyl CoA synthase (FACS), N-acylated phosphatidylethanolamine synthase (NAPE synthase), and NAPE phospholipase-D (NAPE-PLD). In this embodiment, the engineered microbes may produce increased levels of C18:0 FAEs. The method for production of FAEs can include using the engineered microbes may produce increased levels of C18:0 FAEs.

An embodiment of the present subject matter is directed to a pharmaceutical composition including the engineered microbes and a pharmaceutically acceptable carrier.

An embodiment of the present subject matter is directed to a method of making a pharmaceutical composition including mixing the engineered microbes under sterile conditions with a pharmaceutically acceptable carrier and preservatives, buffers, or propellants to create the pharmaceutical composition; and providing the pharmaceutical composition in a form suitable for daily, weekly, or monthly administration.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
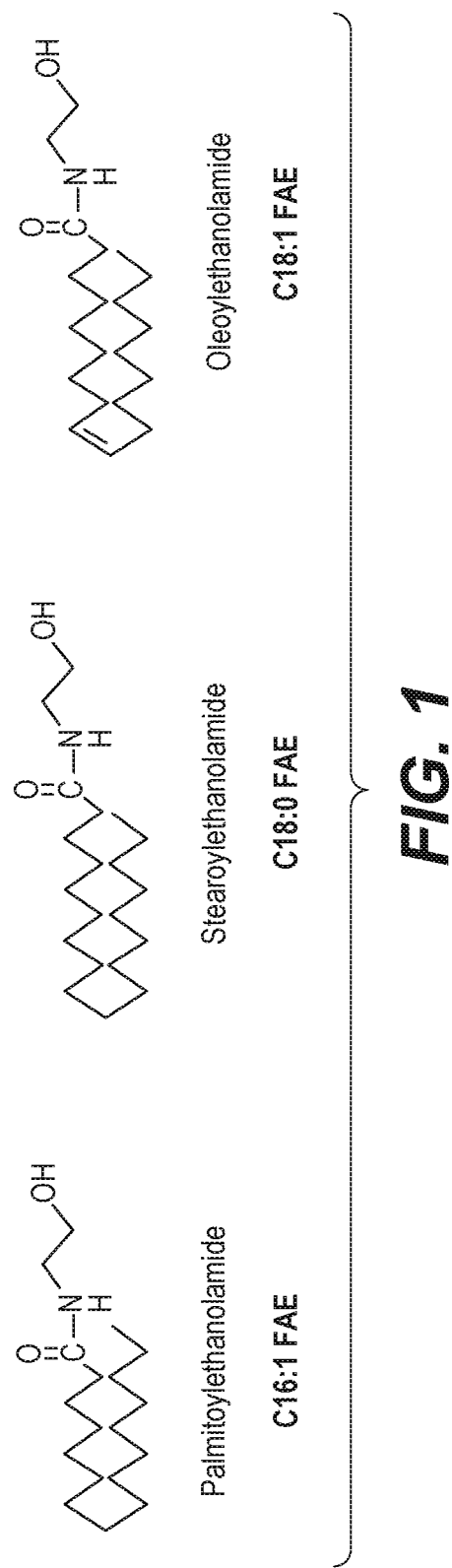
FIG. 1: depicts the chemical structures of fatty acid ethanolamides (FAEs).

A system and method for production of fatty acid ethanolamides (FAEs) provides for in vivo synthesis of FAEs using engineered microbes and food stocks to produce a surplus of FAEs. The microbes are engineered to express the necessary enzymes to complete a biosynthetic pathway, resulting in the conversion of glucose to one or more desired FAEs. The microbes may be grown in a standard bioreactor, fermenter, or under any known optimized growth conditions to allow for synthesis of the one or more desired FAEs. These FAE-producing microbes can be administered to a subject in need thereof as part of a probiotic regimen, or the desired FAEs may be isolated from the FAE-producing microbes and included in a pharmaceutical composition. The FAE-producing microbes may be administered to subjects suffering from any condition that the selected FAE is known to have activity against, including but not limited to subjects suffering from obesity or chronic pain.

As used herein, a "subject" may be any species of animal, including but not limited to human beings.

As used herein, a "microbe" is a single celled organism, such as a bacterium. Suitable microbes include those capable of horizontal gene transfer, allowing for the incorporation of exogenous genetic information, such as information carried on a plasmid, into the microbe's genome.

As used herein, a "plasmid" is a small, extrachromosomal DNA molecule capable of independent replication. Plasmids may be conjugative or non-conjugative. Plasmids may be used to introduce one or more genes capable of expressing one or more proteins into a microbe. The one or more genes may be under the control of one or more inducible or constitutive promoters.

As used herein, "probiotic" refers to a composition including a live microbe that, when ingested by a subject, grows or replicates in the subject's gut, providing a beneficial effect to the subject.

An embodiment of the present subject matter is directed to a pharmaceutical composition comprising the engineered microbes and a pharmaceutically acceptable carrier.

An embodiment of the present subject matter is directed to a method of making a pharmaceutical composition including mixing the engineered microbes with a pharmaceutically acceptable carrier. For example, the method of making a pharmaceutical composition can include mixing the engineered microbes under sterile conditions with a pharmaceutically acceptable carrier, preservatives, buffers, and/or propellants to create the pharmaceutical composition.

An embodiment of the present subject matter is directed to a pharmaceutical composition including the engineered microbes. To prepare the pharmaceutical composition, the engineered microbes, as an active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral, parenteral, intranasal, sublingual or rectal administration, or for administration by inhalation or insufflation. The active compound can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose.

The engineered microbes or pharmaceutical compositions thereof can be administered to a subject by any suitable route. For example, the compositions can be administered orally (including buccally and sublingually), nasally, rectally, intracisternally, intraperitoneally, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

Accordingly, the route of administration can include intranasal administration, oral administration, inhalation administration, subcutaneous administration, intradermal administration, intra-arterial administration with or without occlusion, intracranial administration, intraventricular administration, intravenous administration, buccal administration, intraperitoneal administration, intraocular administration, intramuscular administration, implantation administration, intratumor administration, and/or central venous administration.

In an embodiment, the system for production of FAEs may include *E. coli* microbes engineered to express a thioesterase (TES), fatty acyl CoA synthase (FACS), N-acylated phosphatidylethanolamine synthase (NAPE synthase), and NAPE phospholipase-D (NAPE-PLD). In this embodiment, the engineered microbes may produce increased levels of C18:0 FAEs.

The system and method for production of FAEs may use any microbe that may be engineered to express a FAE-producing pathway. As a non-limiting example, the microbe may be selected from *E. coli, Bacillus subtilis*, or a yeast, such as *Saccharomyces cerevisiae*. The microbe may be selected for the presence of existing metabolic pathways that include FAE precursors. The microbe may also be selected for suitability for use in a probiotic composition.

In an embodiment, a selected microbe may then be engineered to express further components of a FAE-producing pathway. In a non-limiting example, the selected microbes may be transformed with one or more plasmids expressing multiple enzymes involved in FAE synthesis. These enzymes may include thioesterase, fatty acid synthase, fatty acyl CoA synthase, NAPE synthase, and NAPE phospholipase.

FAEs, also known as N-acyl ethanolamines (or NAEs) are amides formed from carboxylic acids and ethanolamine (See FIG. 1). FAEs that may be synthesized by a FAE-producing pathway include but are not limited to palmitoylethanolamide (C16:1 FAE), stearoylethanolamide (C18:0 FAE), and oleoylethanolamide (C18:1 FAE).

Figure 2:
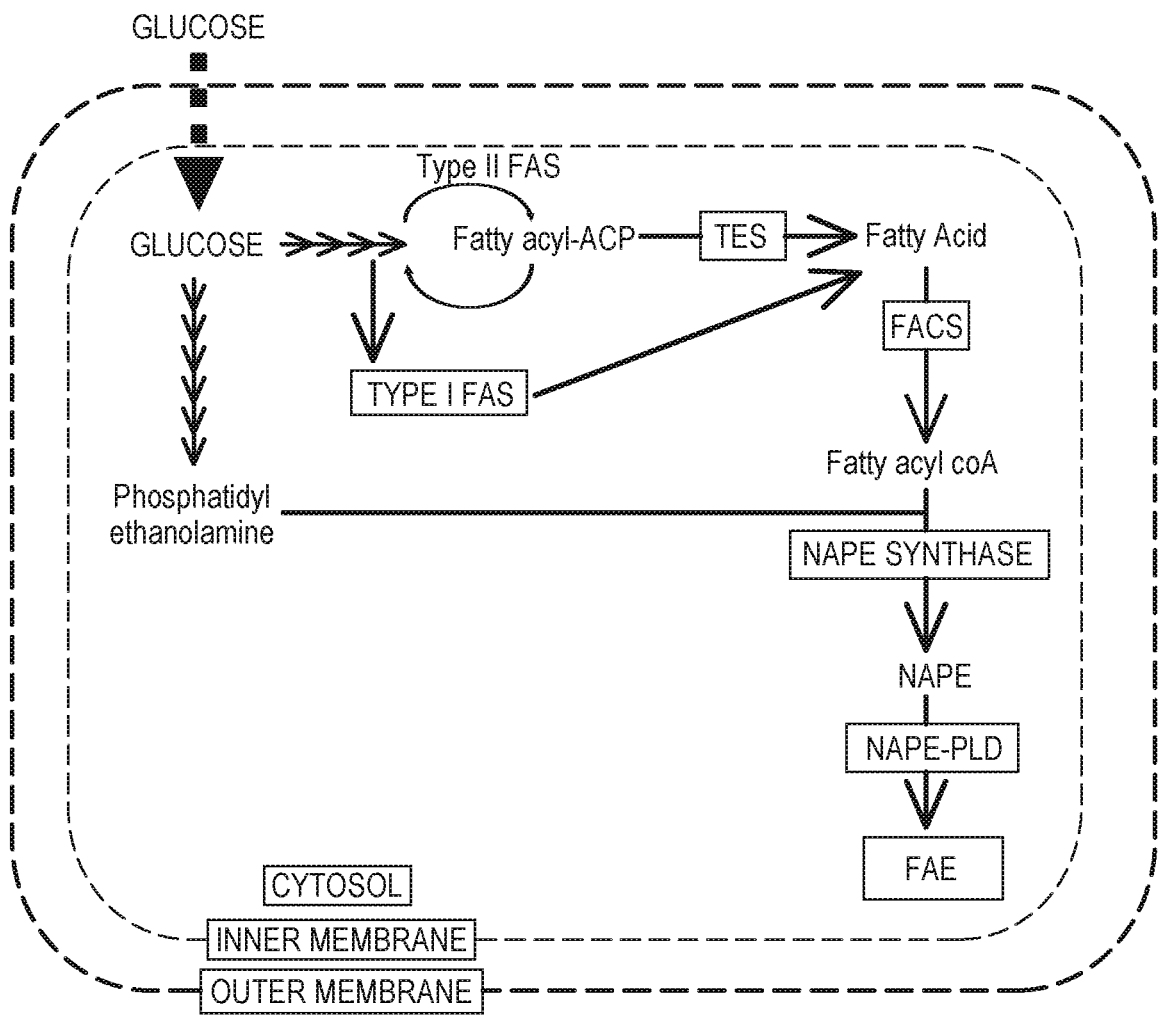
FIG. 2: depicts an overall metabolic scheme for the biological production of FAEs.
Figure 3:
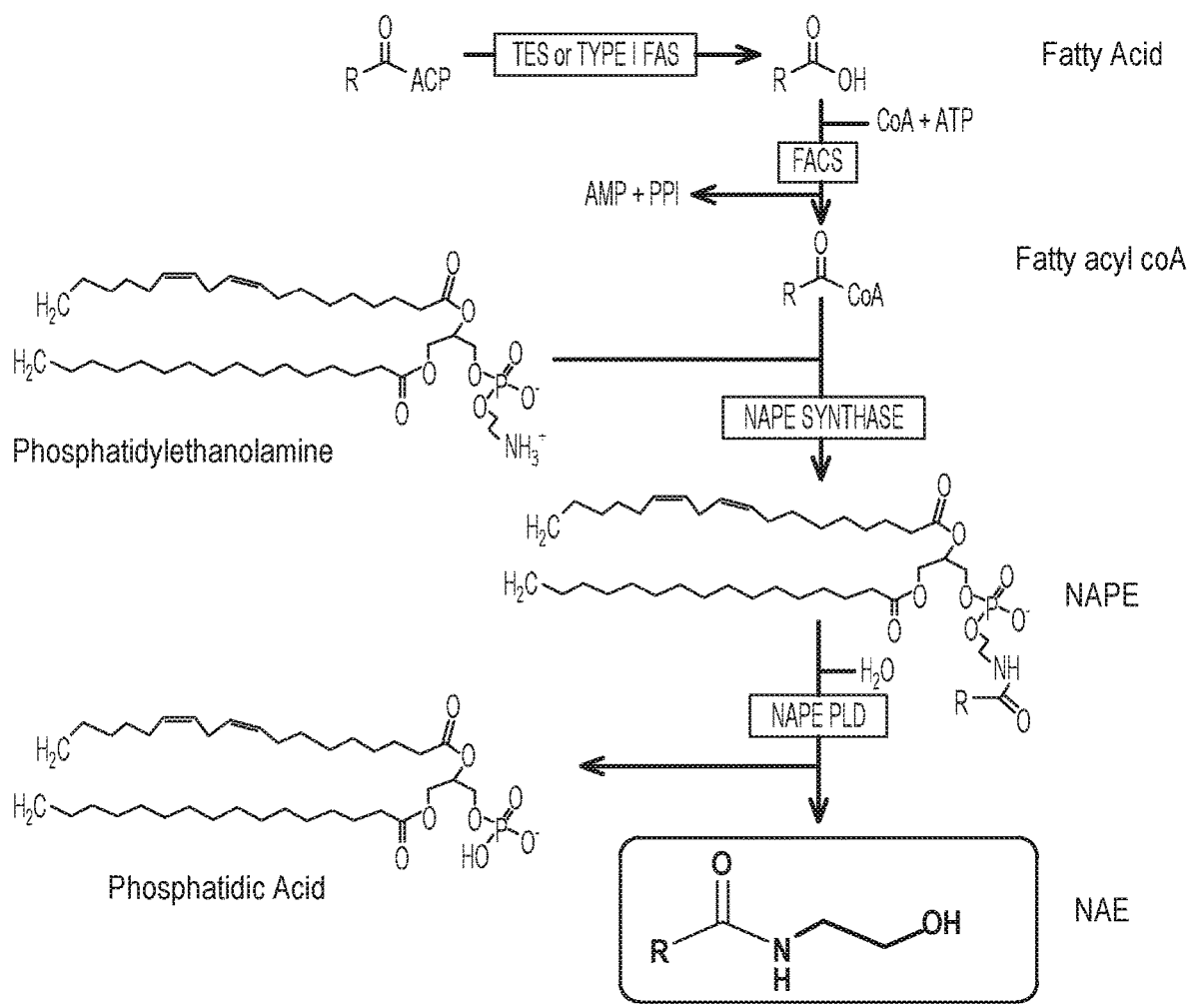
FIG. 3: depicts key enzymes involved in the engineered production of FAEs.

In an embodiment, FAEs may be synthesized using a synthesis pathway that incorporates a particular microbe's naturally occurring precursors to drive FAE synthesis. For example, in *E. coli*, existing metabolic pathways convert glucose to either fatty acyl-ACP or phosphatidyl ethanolamine. In the presence of a thioesterase (TES), the fatty acyl-ACP may be hydrolyzed to fatty acids. The fatty acids may then be activated to fatty acyl CoA by fatty acyl CoA synthase (FACS), which may serve as the fatty acyl donor with naturally produced phosphatidylethanolamine to form N-acylated phosphatidylethanolamine (NAPE) via a reaction catalyzed by NAPE-synthase. NAPE may then be hydrolyzed to form FAE by NAPE phospholipase-D. Thus, *E. coli* engineered to express TES, FACS, NAPE-synthase and NAPE-PLD may produce C18:0 FAE. (See FIGS. 2-3)

The following examples illustrate the present teachings.

Example 1

Cloning and Induction of a Pathway for C18:0 FAE Synthesis in *E. coli*

The genes encoding for thioesterase, fatty acyl CoA synthase, NAPE-synthase and NAPE-PLD were synthesized and subcloned into a T7-based expression plasmid pET duet-1, via NcoI and XhoI restriction sites (GeneScript). The resulting recombinant plasmid was inserted into an *E. coli* expression host, BL21(D3). Expression of the FAE synthesis pathway was induced with 20 μM IPTG. Cells were incubated (18-24 hours, 200 rpm, 28° C.) overnight in minimal media including 2% (w/v) glucose, M9 salts (Sigma Aldrich), 100 mM potassium phosphate buffer, 2 mM $MgSO_4$, 0.1 mM $CaCl_2$), 100 mM $NH_4Cl$ (pH 7.5, 21° C.), metal mix (10 nM $FeSO_4$, 0.4 mM boric acid, 30 μM $CoCl_2$, 15 μM $CuSO_4$, 80 μM $MnCl_2$ and 10 μM $ZnSO_4$) and supplemented with ampicillin for plasmid selection.

Example 2

Confirmation of C18:0 FAE Synthesis in Engineered *E. coli*

Figure 4A:
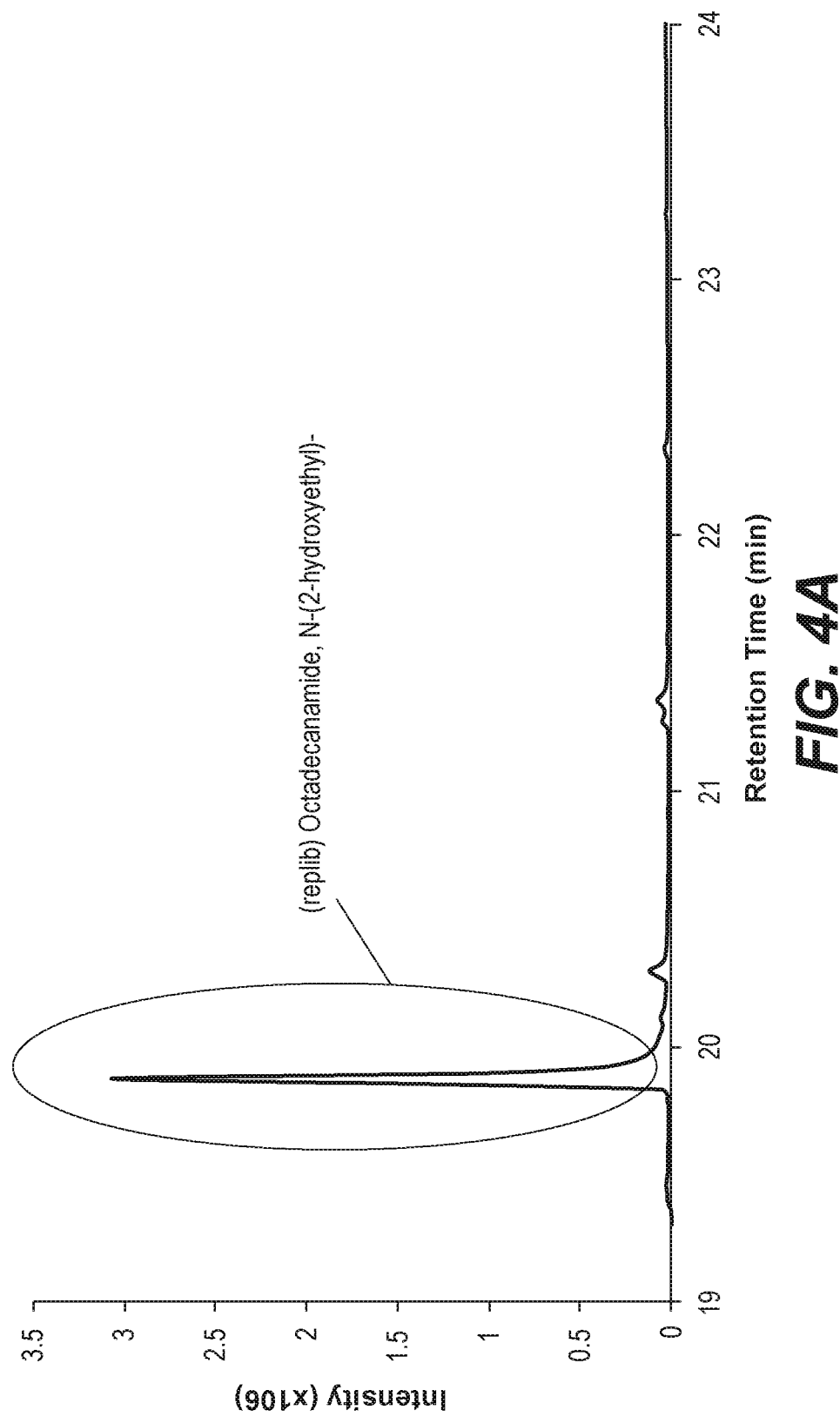
FIG. 4A: depicts a gas chromatogram showing the separation of the C18:0 FAE produced according to the present teachings.
Figure 4B:
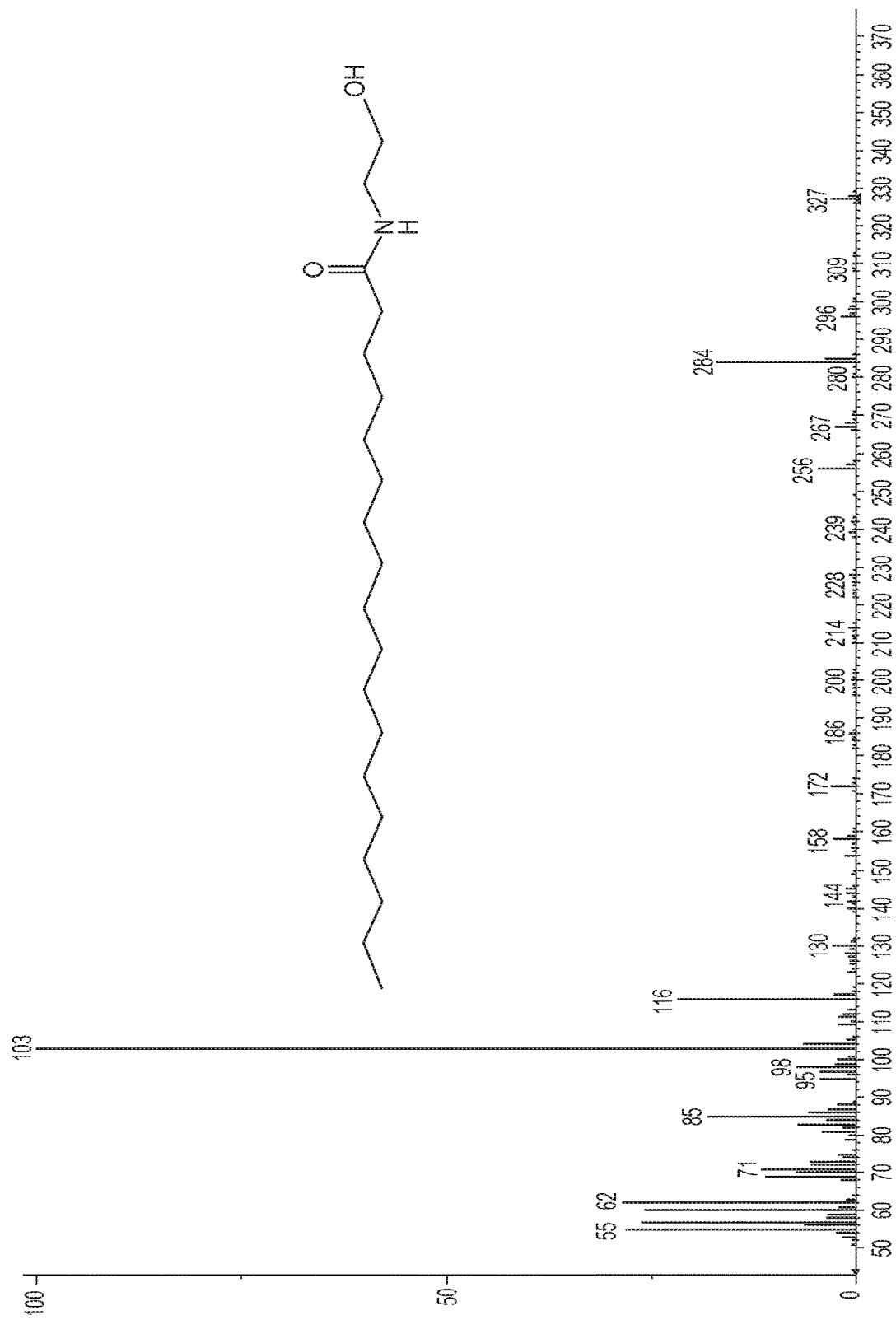
FIG. 4B: depicts a mass spectrum verifying the production of C18:0 FAE.

After synthesis and induction of the engineered *E. coli* as described in Example 1, 1,000 μl of culture extracts were vortexed vigorously with acetonitrile (500 μl). Cell debris were precipitated by centrifugation and the supernatant was transferred to a clean vessel. After drying the supernatant under vacuum in a Speedvac the content was redissolved in 100 μl ethyl acetate. Samples were analyzed by GC-MS (gas chromatograph-mass spectrometry) using a triple quadruple a mass spectrometer. Samples were injected in splitless injection mode (1 μl) with the inlet temperature set at 180° C. and passed through a HP-5 column (Agilent) (30 m×250 μm×0.25 μm) at a flow rate of 1 ml/min, using helium as the carrier gas. The oven was initially held at 180° C. and ramped up to 300° C. Ions were analyzed in the normal MS mode within the 50-370 m/z range. The presence of N-(2-Hydroxyethyl) octadecanamide was confirmed by comparing fragmentation patterns and retention times of the analytes with the NIST mass spectral library and a commercially available standard (Sigma). (See the GC chromatogram (FIG. 4A) and mass spectrum (FIG. 4B))

It is to be understood that the system and method for production of fatty acid ethanolamides is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A system for production of fatty acid ethanolamides, comprising a microbe engineered to express thioesterase, fatty acyl CoA synthase, N-acylated phosphatidylethanolamine synthase, and NAPE phospholipase-D.

2. The system for production of fatty acid ethanolamides as recited in claim 1, wherein the microbe is selected from the group consisting of *E. coli, Bacillus subtilis*, and *Saccharomyces cerevisiae*.

3. The system for production of fatty acid ethanolamides as recited in claim 2, wherein the microbe is *E. coli*.

4. The system for production of fatty acid ethanolamides as recited in claim 1, wherein the microbe produces increased levels of fatty acid ethanolamides.

5. The system for production of fatty acid ethanolamides as recited in claim 4, wherein the microbe produces C18:0 fatty acid ethanolamides.

6. A probiotic composition comprising a microbe engineered to express a fatty acid ethanolamide (FAE)-producing pathway comprising thioesterase, fatty acyl CoA synthase, N-acylated phosphatidylethanolamine synthase, and NAPE phospholipase-D and a pharmaceutically acceptable carrier.

7. The probiotic composition as recited in claim 6, wherein the microbe is selected from the group consisting of *E. coli, Bacillus subtilis*, and *Saccharomyces cerevisiae*.

8. The probiotic composition as recited in claim 7, wherein the microbe is *E. coli*.

9. The probiotic composition as recited in claim 6, wherein the microbe produces C18:0 fatty acid ethanolamides.

10. A method of designing a system for production of fatty acid ethanolamides, comprising: selecting a microbe that naturally produces fatty acid ethanolamide precursors; and genetically engineering the microbe to express a FAE-producing pathway comprising thioesterase, fatty acyl CoA synthase, N-acylated phosphatidylethanolamine synthase, and NAPE phospholipase-D.

11. The method of designing a system for production of fatty acid ethanolamides as recited in claim 10, wherein the microbe is selected from the group consisting of *E. coli, Bacillus subtilis*, and *Saccharomyces cerevisiae*.

12. The method of designing a system for production of fatty acid ethanolamides as recited in claim 11, wherein the microbe is *E. coli*.

13. The method of designing a system for production of fatty acid ethanolamides as recited in claim 10, wherein the microbe produces C18:0 fatty acid ethanolamides.

* * * * *